(12) United States Patent
Anderson et al.

(10) Patent No.: US 7,960,437 B2
(45) Date of Patent: Jun. 14, 2011

(54) SKIN CARE COMPOSITION THAT MEDIATES CELL TO CELL COMMUNICATION

(75) Inventors: Glen T. Anderson, Manor, NY (US); Dmitri S. Ptchelintsev, Jersey City, NJ (US); Gopinathan K. Menon, Wayne, NJ (US); John A. Duffy, West Milford, NJ (US)

(73) Assignee: Avon Products, Inc., New York, NY (US)

( * ) Notice: Subject to any disclaimer, the term of this patent is extended or adjusted under 35 U.S.C. 154(b) by 33 days.

(21) Appl. No.: 11/040,534

(22) Filed: Jan. 21, 2005

(65) Prior Publication Data

US 2005/0129723 A1 Jun. 16, 2005

Related U.S. Application Data

(60) Continuation of application No. 10/198,772, filed on Jul. 19, 2002, now abandoned, which is a division of application No. 09/812,707, filed on Mar. 20, 2001, now abandoned, which is a continuation-in-part of application No. 09/461,449, filed on Dec. 14, 1999, now abandoned.

(60) Provisional application No. 60/190,988, filed on Mar. 21, 2000.

(51) Int. Cl.
*A61K 31/045* (2006.01)
*A61K 31/34* (2006.01)
*A61K 31/7076* (2006.01)
*A61K 35/00* (2006.01)
*A61K 36/00* (2006.01)
*A61K 38/01* (2006.01)
*A61P 17/00* (2006.01)

(52) U.S. Cl. .............. 514/739; 424/195.17; 424/520; 424/764; 424/780; 514/18.8; 514/47; 514/461; 514/473; 514/938

(58) Field of Classification Search .............. None
See application file for complete search history.

(56) References Cited

U.S. PATENT DOCUMENTS

| 3,978,213 A | * | 8/1976 | Lapinet et al. ............ 514/47 |
| 4,496,536 A | * | 1/1985 | Moller et al. ............ 424/70.8 |
| 5,314,873 A | * | 5/1994 | Tomita et al. ............ 514/21 |

FOREIGN PATENT DOCUMENTS

| JP | 60-214722 | | 10/1985 |
| JP | 4-26604 | | 1/1992 |
| JP | 5-503522 | | 6/1993 |
| JP | 6-166615 | | 6/1994 |
| JP | 9-30946 | | 2/1997 |
| JP | 09-030946 A | | 2/1997 |
| JP | 10-29927 | | 2/1998 |
| JP | 10-114648 | | 5/1998 |
| JP | 10-167957 | | 6/1998 |
| WO | WO 91/11169 | | 8/1991 |
| WO | 96/17605 | | 6/1996 |
| WO | WO 9617605 A1 | * | 6/1996 |
| WO | WO 9727835 A1 | * | 8/1997 |

OTHER PUBLICATIONS

STN/CAS online, file CAPLUS, Acc. No. 1999:495147, Doc. No. 131:134413, (COTY B.V., Neth., WO 9938483 A (Aug. 5, 1999), 'Cosmetic product based on *Artemia salia* extract for regenerating and stimulating skin cells'), Abstract.*

STN/CAS online, file CAPLUS, Acc. No. 1998:580363, Doc. No. 129:206991, (Parfuem. Kosmet. (1998), vol. 79, No. 7/8, pp. 14-16), Abstract.*

STN/CAS online, file CAPLUS, Acc. No. 1992:425089, Doc. No. 117:25089, (Dainippon Ink and Chemicals, Inc., Japan, WO 9204420 A (Mar. 19, 1992), 'Sunflower seed extract as antioxidant'), Abstract.*

* cited by examiner

*Primary Examiner* — John Pak
*Assistant Examiner* — Frank Choi
(74) *Attorney, Agent, or Firm* — Charles J. Zeller; Jean M. McGillycuddy

(57) ABSTRACT

There are disclosed skin treatment compositions containing cell signaling compounds, which induce and promote the biosynthesis and/or bioactivity of endogenous chemicals that mediate cell to cell communication in the skin between keratinocytes, fibroblasts and other cell types present in the skin. The cell signaling compound is selected from the group consisting of: andrographolide and its derivatives; adenosine cyclic phosphate and its derivatives; hydrolyzed milk proteins; sunflower seed extract; plankton extract; phytol and its derivatives; and mixtures thereof.

10 Claims, No Drawings

SKIN CARE COMPOSITION THAT MEDIATES CELL TO CELL COMMUNICATION

RELATED APPLICATIONS

This application is a continuation of U.S. application Ser. No. 10/198,772, filed on Jul. 19, 2002 now abandoned, which is a divisional of U.S. application Ser. No. 09/812,707 filed on Mar. 20, 2001 now abandoned which is a continuation-in-part of U.S. application Ser. No. 09/461,449 filed on Dec. 14, 1999 now abandoned. Priority is also claimed from U.S. Provisional Patent Application Ser. No. 60/190,988 filed on Mar. 21, 2000 and PCT Patent Application Serial No. PCT/US00/33776 filed on Dec. 14, 2000.

BACKGROUND OF THE INVENTION

1. Field of the Invention

The present invention relates to cosmetic compositions. More particularly, the present invention relates to an emulsified skin treatment or skin care composition containing certain compounds that have been found highly effective in mediating cell to cell communication.

The present invention is based on the discovery that certain compounds, when formulated into a composition designed for topical application to the skin, will result in a composition that induces and promotes the biosynthesis and/or bioactivity of endogenous chemicals. The chemicals mediate cell to cell communication in the skin between keratinocytes, fibroblasts and other cell types present in the skin by activating gene expression which, in turn, enhances cellular activity. As a result, anti-aging and skin normalizing benefits can be achieved because the enhanced cellular communication stimulates sluggish cellular activity normally seen in older cells and reprograms skin to behave like younger skin. In short, it may help to turn skin "on" where it is "off".

2. Description of the Prior Art

U.S. Pat. No. 5,686,489 issued on Nov. 11, 1987 to Yu et al. It discloses the use of alkyl esters of alpha-hydroxy acids to increase skin thickness when topically applied to the skin in a composition having a concentration range of 1 to 100%, preferably about 2 to 5%.

U.S. Pat. No. 3,978,213 issued on Aug. 31, 1976 to Lapinet et al. and discloses the use of cyclic 3',5'-adenosine monophosphate (cyclic AMP) as a skin softening agent which can be applied to the skin at concentrations of 0.01-2% in the form of lotions and creams, including oil in water emulsions.

U.S. Pat. No. 5,362,494, which issued on Nov. 8, 1994 to Zysman et al., discloses a particular surfactant for preparing skin treatment compositions that may also contain cyclic AMP, plankton and sunflower oil.

U.S. Pat. No. 5,741,518 issued on Apr. 21, 1998 to Ribler et al. and U.S. Pat. No. 5,626,868 issued on May 6, 1997 to Morancais et al. Both patents disclose skin treatment compositions in the form of a dispersion of vesicles and list cyclic AMP and plankton among many optional functional ingredients.

U.S. Pat. No. 5,314,873 issued on May 24, 1994 to Tomita et al. This patent provides a milk-protein hydrolyzate that consists of a mixture of peptides and free amino acids. The mixture has proliferation activating properties on human cutaneous cells. The peptides of the hydrolyzate have molecular weights less than 1000 daltons. The hydrolyzate has a free aromatic amino acid/total aromatic amino acid ratio of at least 90%. Fractionation of the milk protein hydrolyzate yields a fraction consisting of a mixture of peptides. The fraction has a proliferation activating property on human cutaneous cells. The fraction contains aromatic amino acids in an amount less than 5% by weight of total amino acids. It is disclosed for use in skin care emulsions.

U.S. Pat. No. 5,484,597 issued on Jan. 16, 1996 to Slavtcheff et al., and discloses a hydroalcoholic microemulsion composition for skin treatment. The composition includes water, a $C_1$-$C_4$ alkanol and an oil material selected from vitamin oils, $C_{10}$-$C_{60}$ terpenes and mixtures thereof. The composition is formed into a clear, storage stable microemulsion through a combination of surfactants including an ethoxylated castor oil and a propoxylated alkyl ether. The terpene may be an oxygenated terpene such as phytol.

SUMMARY OF THE INVENTION

It is an object of the present invention to provide a cosmetic composition effective in mediating cell to cell communication.

It is another object of the present invention to provide such a composition that mediates cell to cell communication in the skin between keratinocytes, fibroblasts and other cell types present in the skin.

It is a further object of the present invention to provide such a composition that produces anti-aging and skin normalizing benefits by rejuvenating the cellular processes in skin.

It is still a further object of the present invention to provide such a composition in which the anti-aging and skin normalizing benefits include, but are not limited to, reduction of wrinkles, reduction of fine lines, reduction in skin blotchiness, improvements in skin mechanical and tactile properties such as smoothness, texture, moisture, elasticity and resiliency, and improvements in skin color, clarity, tone and aesthetic appearance, including size and number of pores.

These and other objects of the present invention will be achieved by a topical composition comprising effective amounts of a cell signaling compound, said cell signaling compound being selected from the group consisting of:

(a) andrographolide and its derivatives of the formula:

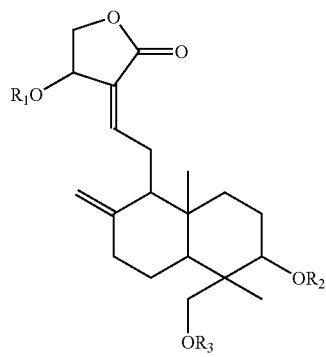

where $R_1$, $R_2$ and $R_3$ can independently represent hydrogen, acyl, phenyl, mono- or polyphosphate, mono- or polysulfate, glycosyl, cyclic or acyclic alkyl, alkenyl or alkynyl, wherein said phosphate or sulfate derivatives may be in the form of free acids or as salts with counter-cations selected from the group consisting of lithium, sodium, potassium, ammonium, magnesium, strontium and barium;

(b) adenosine 3',5'-monophosphate and its derivatives of the formula:

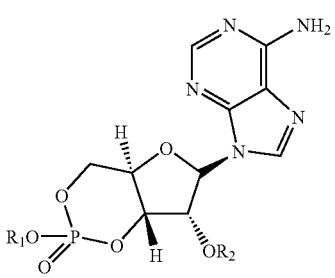

where $R_1$ and $R_2$ can independently represent hydrogen, acyl, phenyl, mono- or polyphosphate, mono- or polysulfate, glycosyl, cyclic or acyclic alkyl, alkenyl or alkynyl, wherein said phosphate or sulfate derivatives may be in the form of free acids or as salts with counter-cations selected from the group consisting of lithium, sodium, potassium, ammonium, magnesium, strontium and barium;

(c) hydrolyzed milk protein;
(d) sunflower seed extract;
(e) plankton extract;
(f) phytol, and its derivatives of the formula:

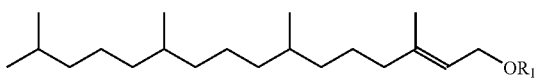

where $R_1$ can represent hydrogen, acyl, phenyl, mono- or polyphosphate, mono- or polysulfate, glycosyl, alkyl, alkenyl or alkynyl, wherein said phosphate or sulfate derivatives may be in the form of free acids or as salts with counter-cations selected from the group consisting of lithium, sodium, potassium, ammonium, magnesium, strontium and barium; and (g) mixtures thereof.

Preferably, the composition includes at least two and, more preferably, at least three cell signaling compounds.

DETAILED DESCRIPTION OF THE INVENTION

In accordance with the present invention, there has been discovered a topical cosmetic comprising an effective amount a cell signaling compound. Preferably, the composition is an effective amount of at least two or three cell signaling compounds of the group of six described below. More preferably, the composition includes phytol, either alone or in combination with at least one other of the cell signaling compounds.

The cell signaling compounds induce and promote the biosynthesis and/or bioactivity of endogenous chemicals that mediate cell to cell communication in the skin between keratinocytes, fibroblasts and other cell types present in the skin.

The endogenous chemicals that are effected by cell to cell communication include growth and differentiation hormones, releasing hormones, neurotransmitters, nucleotides and nucleosides, bioactive carbohydrates, enzymes and enzyme cofactors, mono- and polyphosphates of deoxyadenosine, deoxythymidine, deoxycytidine, inositol phosphates, and other ion channel modulators, adenyl cyclase, messenger, ribosmal and transfer ribonucleic acids, stress proteins, mono- and polyphosphates of adenosine, deoxyribonucleic acid, adenosine 3',5'-monophosphate, guanosine 3',5'-monophosphate, effectors of membrane associated receptors including kinases, protein-tyrosine kinases, protein-serine/threonine kinases, protein phosphatases, small G-proteins, GDP/GTP exchange and guanosine nucleotide releasing factors and transcription factors.

Six cell signaling compounds have been found useful in forming the compositions of the present invention. The first such cell signaling compound is andrographolide and its derivatives of the formula:

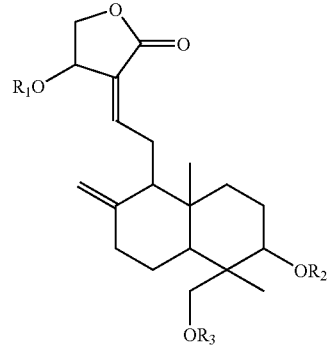

where $R_1$, $R_2$ and $R_3$ can independently represent hydrogen, acyl, phenyl, mono- or polyphosphate, mono- or polysulfate, glycosyl, cyclic or acyclic alkyl, alkenyl or alkynyl having 1 to 16 carbon atoms. The phosphate or sulfate derivatives may be in the form of free acids or as salts with counter-cations selected from lithium, sodium, potassium, ammonium, magnesium, strontium or barium. Andrographolide is available commercially from Alchem International Ltd. It is present in an amount about 0.001 percentage by weight or weight percent (wt %) to 1 wt %, preferably 0.005 wt % to 0.1 wt %, more preferably about 0.01 to about 1.0 wt %, and most preferably about 0.1 wt % of the total weight of the composition.

The second cell signaling compound is adenosine 3',5'-monophosphate and its derivatives of the formula:

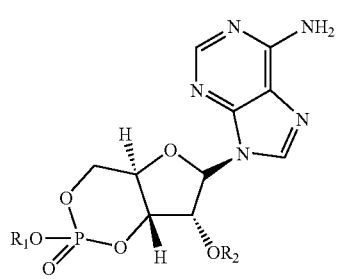

where $R_1$ and $R_2$ can independently represent hydrogen, acyl, phenyl, mono- or polyphosphate, mono- or polysulfate, glycosyl, cyclic or acyclic alkyl, alkenyl or alkynyl having 1 to 16 carbon atoms. The phosphate or sulfate derivatives may be in the form of free acids or as salts with counter-cations selected from a group of lithium, sodium, potassium, ammonium, magnesium, strontium and barium. Adenosine 3',5'-monophosphate is available commercially as cAMP from Pharma-Waldhof GmbH. The second cell signaling compound is present in an amount about 0.0001 wt % to about 1 wt %, preferably 0.0005 wt % to 0.1 wt %, more preferably about 0.001 wt % to about 1.0 wt %, and most preferably about 0.01 wt % of the total weight of the composition.

The third cell signaling compound is hydrolyzed milk protein. It is available commercially as Hydrakine from Bioetica, Inc. It is present in an amount about 0.01 wt % to about 10 wt %, preferably about 0.1 wt % to about 5 wt %, and most preferably about 0.5 wt % of the total weight of the composition.

The fourth cell signaling compound is sunflower (*helianthus annuus*) seed extract. It is available commercially as Antiglyskin from Silab. It is present in an amount about 0.01 wt % to about 10 wt %, preferably about 0.1 wt % to about 5 wt %, and most preferably about 0.5 wt % of the total weight of the composition.

The fifth cell signaling compound is plankton (*aretemia*) extract. A preferred component of plankton extract is diguanosine tetraphosphate. Diguanosine tetraphosphate is available commercially as GP4G from M.M.P., Inc. It is present in an amount about 0.01 wt % to about 10 wt %, preferably about 0.1 wt % to about 5 wt %, and most preferably about 0.5 wt % of the total weight of the composition.

The sixth cell signaling compound is phytol, and derivatives thereof having the formula:

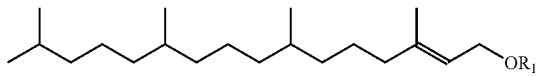

where $R_1$ can represent hydrogen, acyl, phenyl, mono- or polyphosphate, mono- or polysulfate, glycosyl, alkyl, alkenyl or alkynyl, wherein said phosphate or sulfate derivatives may be in the form of free acids or as salts with counter-cations selected from the group consisting of lithium, sodium, potassium, ammonium, magnesium, strontium and barium. The phosphate or sulfate derivatives may be in the form of free acids or as salts with counter-cations and may be lithium, sodium, potassium, ammonium, magnesium, strontium or barium. Phytol is available from BASF Corporation. The sixth cell signaling compound is present in an amount from about 0.0001 wt % to about 50 wt %, preferably from about 0.01 wt % to about 20 wt %, and more preferably from about 0.1 wt % to about 15 wt %, still more preferably about 0.01 wt % to about 5.0 wt %, and most preferably about 1.0 wt % of the total weight of the composition.

The total amount of cell signaling compounds used in any composition is about 0.1 wt % to about 20 wt %, preferably about 0.5 wt % to about 5 wt %, of the total weight of the composition.

In the more preferred embodiment, at least two or three of the six cell signaling compounds are present in the composition. It is also preferred that four or all five of the cell signaling compounds are present. The preferred combinations of cell signaling compounds include: (1) hydrolyzed milk protein and sunflower seed extract; (2) hydrolyzed milk protein, sunflower seed extract and plankton extract; (3) hydrolyzed milk protein, sunflower seed extract and andrographolide and its derivatives; (4) hydrolyzed milk protein, sunflower seed extract and adenosine 3',5'-monophosphate and its derivatives; (5) sunflower seed extract and andrographolide and its derivatives; (6) sunflower seed extract and adenosine 3',5'-monophosphate and its derivatives; phytol and its derivatives.

The composition may be in the form of gels, lotions, serums, anhydrous sticks, oil based sprays, oil-in-water emulsions or water-in-oil emulsions.

The present emulsion or composition may include other ingredients. For example, water will typically comprise about 40 wt % to about 80 wt %, preferably about 40 wt % to about 55 wt %, and most preferably about 45 wt % to about 50 wt %, of the total weight of the composition.

The composition may also have at least one emulsifier. The emulsifier may be anionic, nonionic, cationic, amphoteric or zwitterionic. Suitable emulsifiers include polymeric acrylate emulsifiers, polyethylene glycol 20 sorbitan monolaurate (Polysorbate 20), polyethylene glycol 5 soya sterol, sorbitan tristearate, polyethyleneglycol 40 stearate, sorbitan trioleate, glyceryl, monopalmitate, diethanolamine cetyl phosphate, glyceryl monopalmitate, glyceryl monostearate, polyethylene glycol 100 stearate, polyethylene glycol 20 stearyl ether (Brij 78, Steareth 20), polyethylene glycol ether of lauryl alcohol (Laureth 23), polysorbate 80 (Tween 80), lecithin, etc. The composition will preferably contain a mixture of two or more of these emulsifiers or others which are approved for cosmetic use. The total amount of emulsifier will vary from about 0.1 wt % to about 10 wt %, of the total weight of the composition, preferably about 1 wt % to about 5 wt %.

The composition should have at least one preservative. Suitable preservatives include benzyl alcohol, ethanol, 2-phenoxyethanol, disodium EDTA (ethylenediamine tetraacetic acid), methyl paraben, ethyl paraben, butyl paraben, imidazolidinyl urea and the like commonly known to prevent bacteria growth and typically in the range of about 0.1 wt % to about 3 wt %, of the total weight of the composition.

The composition of the present invention may contain one or more other ingredients. For example, the compositions of the present invention will typically contain conventional cosmetic ingredients necessary in formulating a desirable product. In addition to water, suitable inorganic thickeners may be used. Such inorganic thickeners include clays, such as bentonite, hectorite, kaolin, and montmorillonite; and metal silicates, such as calcium silicate, aluminum silicate and preferably magnesium aluminum silicate. They are employed in amounts about 0.01 wt % to about 5 wt %, preferably about 0.2 wt % to about 2.0 wt %, and most preferably about 0.4 wt %, of the total weight of the composition.

The composition may have an organic thickener to ensure that it has the proper viscosity when applied to the skin. Examples of such thickeners, which may be used, include hydroxyethyl cellulose, carboxymethyl cellulose, xanthan gum, polyacrylamide (Seppi Gel 305), Carbopol 934, Carbopol 940, Carbopol 950, Carbopol 980, Carbopol 951 and Carbopol 981. The amount of such organic thickener is typically in the range about 0.01 wt % to about 5 wt %, preferably about 0.1 wt % to 1.5 wt %, and most preferably about 0.8 wt %, of the total weight of the composition.

The compositions of the present invention may contain one or more sunscreens or UV (ultraviolet) absorbing agents. Examples of such sunscreens in preferred amounts are:

| Sunscreen | Percentage (wt %) |
|---|---|
| oxybenzone | 2 to 10 |
| sulsiobenzone | 5 to 10 |
| dioxybenzone | 1 to 3 |
| menthyl anthranilate | 3 to 6 |
| para aminobenzoic acid (PABA) | 5 to 15 |
| dea methoxycinnamate | 8 to 10 |
| octocrylene | 7 to 10 |
| octyl methoxycinnamate* | 2 to 10 |
| octyl salicylate | 3 to 5 |
| homomenthyl salicylate | 4 to 15 |
| octyl dimethyl PABA | 1.4 to 5 |
| tea salicylate | 5 to 12 |
| titanium dioxide | 2 to 25 |
| zinc oxide | 2 to 25 |
| phenylbenzimidazole sulfonic acid | 1 to 4 |

-continued

| Sunscreen | Percentage (wt %) |
|---|---|
| butylmethoxy dibenzoylmethane** | 0.1 to 5 |
| 4-methyl benzilidene camphor | 0.1 to 6 |
| octyl triazone | 0.1 to 10 |
| terephthalydidene dicamphor sulfonic acid and salts thereof*** | 0.1 to 5 |
| ethyl PABA | 1 to 10 |
| 2-(2'hydroxy-5'-methylphenyl) benzotriazole**** | 0.5 to 10 |
| methylene bis-benzotriazolyl tetramethylbutylphenol***** | 1 to 10 |
| bis-octoxyphenol methoxphenyl triazine****** | 1 to 10 |

*The term "octyl methoxycinnamate" and "ethylhexyl methoxycinnamate" are used interchangeably.
**A non-limiting example of butylmethoxy dibenzoylmethane is available from Givaudan under the tradename "PARSOL 1789".
***A non-limiting example of terephthalydidene dicamphor sulfonic acid and salts thereof is available from L'Oreal under the tradename "MEXORYL SX".
****A non-limiting example of 2-(2'hydroxy-5'-methylphenyl) benzotriazole is available from Ciba-Geigy under the tradename "TINUVIN P".
*****A non-limiting example of methylene bis-benzotriazolyltetramethylbutylphenol is available from Ciba-Geigy under the tradename "TINOSORB-M".
******A non-limiting example of bis-octoxyphenol methoxphenyl triazine is available from Ciba-Geigy under the tradename "TINOSORB-S".

The composition may contain an antioxidant, such as gamma oryzanol (a ferulic acid ester of cycloartenol), mixed tocopherol (a mixture of isomers of Vitamin E), ascorbyl monopalmitate, ascorbyl phosphoryl cholesterol, butylated hydroxy toluene, tomato extract (a natural extract which contains lycopene), or rosemary extract (*Rosmarinus officinalis*). Preferably, the antioxidant is present in an amount about 0.01 wt % to about 5.0 wt % of the total weight of the composition.

The compositions of the present invention may also contain about 1 wt % to about 20 wt % of a humectant, preferably about 1 wt % to about 10 wt %. The most preferred humectant is glycerin and in an amount about 7.5 wt %. Other suitable humectants include sorbitol, sodium 2-pyrrolidone carboxylate, hyaluronic acid and its salts, collagen, glyceryl polymethacrylate, ethoxylate or propoxylate of glucose, polyethylene glycol (for example, Carbowax 400), propylene glycol and butylene glycol.

One or more emollients may also be present in the present composition in an amount about 4 wt % to about 20 wt %. Suitable emollients or oleaginous materials include mineral oil, petrolatum, glyceryl monooleate, myristyl alcohol, isopropyl palmitate, avocado oil, alkyl esters of lactic acid, squalane, octyl palmitate, cocoa butter, sesame oil, propylene glycol dicaprylate/dicaprate, $C_{12}$-$C_{15}$ alcohol esters of benzoic acid, dicaprylyl maleate, isopropyl myristate, diisopropyl dimerate (that is, the diester of isopropyl alcohol and dimer acid), dimethicone, stearoxydimethicone, octyl dodecanol, octyl dodecyl neopentanoate, neopentyl glycol dioctanoate, and hydrogenated polydecene. The preferred emollients are petrolatum, octyl dodecanol, octyl dodecyl neopentanoate, neopentyl glycol dioctanoate, and hydrogenated polydecene, which also function as occlusivity agents.

The present composition may also include one or more insect repellents. Such insect repellents include oil of citronella, Deet, and ethyl 3-(N-butylacetamino) propionate. The preferred insect repellent is ethyl 3-butylacetamino) propionate. This material is sold under the commercial name Merck IR3535, by Merck Corporation. This preferred insect repellent is preferably present in an amount about 5 wt % to about 20 wt % of the total weight of the composition.

One or more exfoliants can be included in the present composition. Such exfoliants include alpha hydroxy acid, beta hydroxy acid, keto acid, oxa acid, oxa diacid, and mixtures thereof. If the exfoliant is alpha hydroxy acid, it is present in an amount about 2 wt % to about 10 wt %, preferably about 5 wt %. If the exfoliant is either oxa acid or oxa diacid or a combination of both, it is preferably present in an amount about 5 wt % to about 10 wt %, of the total weight of the composition.

The present composition may also include panthenol (pro-vitamin B-5) and fructose 1,6 diphosphate. Panthenol stimulates proliferation of fibroblast cells and aids in tissue repair. Fructose 1,6 diphosphate is used at from about 0.01 to about 1.0 wt.% and most preferably at 0.01 wt % based upon the weight of the composition. Fructose 1,6 diphosphate, trisodium salt is available commercially from Roche Diagnostics GmbH.

The present composition may include one or more bodying or thickening agents, such as stearic acid and glyceryl monostearate; and pH adjustors, such as ammonium hydroxide, each in an amount about 0.01 wt % to about 10 wt % and preferably about 1 wt % to about 5 wt %; one or more coloring agents or pigments, such as iron oxides and organic dyes, that total about 0.001 wt % to about 1 wt %; and one or more skin protecting agents, such as dimethyl polysiloxane or panthenol, in an amount about 0.1 wt % to about 5 wt %.

The present composition may be applied to the skin as often as needed. The composition is preferably applied once or twice per day. The composition is targeted and self-adjusting (works only where needed).

The present invention is illustrated by the following example of a skin care and treatment composition (percentages are by weight):

| Wt % | Ingredient |
|---|---|
| 60 | water |
| 0.2 | disodium EDTA |
| 0.8 | Carbopol 934 |
| 0.75 | glyceryl monostearate |
| 1.0 | steareth-2 |
| 1.0 | PEG-40 stearate |
| 0.5 | behenyl alcohol |
| 1.0 | benzyl alcohol |
| 0.2 | methyl paraben |
| 1.0 | sunflower seed extract |
| 1.0 | hydrolyzed milk protein |
| 0.1 | adenosine cyclic phosphate (cAMP) |
| 0.1 | andrographolide |
| 1.0 | plankton extract |
| q.s. | conventional antioxidants, sunscreens, humectants, emollients, pH adjustors, masking agents and coloring agents. |

Compositions of the present invention were applied to the skin of human test panel subjects (the panelists). The skin was examined by a dermatologist and effects were noted.

Part 1

In 2 weeks, 56% of panelists showed an improvement in surface texture.

In 2 weeks, 56% of panelists showed an improvement in skin translucency.

In 2 weeks, 50% of panelists showed an improvement in even skin tone.

In 4 weeks 100% of panelists showed an improvement in surface texture.

In 4 weeks, 100% of panelists showed an improvement in skin translucency.

In 4 weeks, 100% of panelists showed an improvement in even skin tone.

In 4 weeks, 100% of panelists showed an improvement in rosy glow.
In 4 weeks, 100% of panelists showed an improvement in overall appearance.
In B weeks, 84% of panelists showed an improvement in mottled pigment.
In 8 weeks, 100% of panelists showed an improvement in fine wrinkling.
In 8 weeks, 93% of panelists showed an improvement in pores.
In 12 weeks, 70% of panelists showed an improvement in discrete pigment.
In 12 weeks, 53% of panelists showed an improvement in skin suppleness.
Part 2
In 4 weeks, an independent dermatologist saw a 47% improvement in skin texture.
In 8 weeks, an independent dermatologist saw a 62% improvement in skin texture.
In 12 weeks, an independent dermatologist saw a 70% improvement in skin texture.
In 4 weeks, an independent dermatologist saw a 47% improvement in translucency.
In 8 weeks, an independent dermatologist saw a 61% improvement in translucency.
In 12 weeks, an independent dermatologist saw a 70% improvement in translucency.
In 4 weeks, an independent dermatologist saw a 42% improvement in even skin tone.
In 5 weeks, an independent dermatologist saw a 57% improvement in even skin tone.
In 12 weeks, an independent dermatologist saw a 66% improvement in even skin tone.
In 4 weeks, an independent dermatologist saw a 43% improvement in rosy glow.
In 8 weeks, an independent dermatologist saw a 66% improvement in rosy glow.
In 12 weeks, an independent dermatologist saw a 65% improvement in rosy glow.
In 4 weeks, an independent dermatologist saw a 20% reduction in the size of pores.
In 8 weeks an independent dermatologist saw a 28% reduction in the size of pores.
In 12 weeks, an independent dermatologist saw a 29% reduction in the size of pores.
In 4 weeks, an independent dermatologist saw a 23% reduction in fine wrinkling.
In 8 weeks, an independent dermatologist saw a 36% reduction in fine wrinkling.
In 12 weeks, an independent dermatologist saw a 42% reduction in fine wrinkling.
In 4 weeks, an independent dermatologist saw a 31% improvement in overall appearance.
In 8 weeks, an independent dermatologist saw a 41% improvement in overall appearance.
In 12 weeks, an independent dermatologist saw a 46% improvement in overall appearance.
Preferred compositions of the present invention afford the following enhancements for the skin upon regular application to the skin:
One Week
Reduces the appearance of fine lines and wrinkles.
Instantly makes skin look younger, more vibrant.
Helps skin retain its firmness.
Improves skin elasticity.
Helps skin retain its elasticity.
Improves skin resiliency of skin.
Makes skin look younger.
Helps skin stimulate its natural defenses.
Helps skin regulate its moisture level.
Makes skin look smooth.
Improves overall appearance of skin within one week.
Two Weeks
Demonstrates improvement in surface texture.
Demonstrates improvement in skin translucency.
Demonstrates improvement in even skin tone.
Four Weeks
Demonstrates improvement in surface texture for 100% of panelists.
Demonstrates improvement in rosy glow for 100% of panelists.
Demonstrates reduction in size of pores for 100% of panelists.
Demonstrates reduction in face wrinkling for 100% of panelists.
Demonstrates improvement in overall appearance for 100% of panelists.
Eight Weeks
Demonstrates improvement in mottled pigment.
Demonstrates improvement in face wrinkling.
Demonstrates improvement in pores.
Twelve Weeks
Demonstrates improvement in discrete pigment.
Demonstrates improvement in skin suppleness.
The present invention having been described with particular reference to the preferred forms thereof, it will be obvious that various changes and modification may be made herein without departing from the spirit and scope of the present invention as defined by the appended claims.

What is claimed is:

1. A method of treating wrinkles and fine lines on the skin, comprising topically applying to an area of the skin in need thereof an effective amount of a composition comprising
a) a cosmetically acceptable carrier,
b) a first compound of phytol,
c) a second compound of a sunflower seed extract, and
d) a third compound of andrographolide.
2. The method of claim 1, wherein the composition is an oil-in-water emulsion.
3. The method of claim 1, wherein the first, second, and third compounds are present in the composition from about 0.1 wt % to about 2.5 wt % based on the total weight of the composition.
4. The method of claim 1, wherein the composition further comprises a fourth compound of a plankton extract.
5. The method of claim 1, wherein the composition further comprises a fourth compound of adenosine 3',5'-monophosphate.
6. The method of claim 1, wherein the composition further comprises a fourth compound of a hydrolyzed milk protein.
7. The method of claim 1, wherein the composition is topically applied daily for at least one week.
8. The method of claim 1, wherein phytol is present in an amount of from about 0.0001 to about 5%.
9. The method of claim 1, wherein the sunflower seed extract is present in an amount of from about 0.01 to about 5%.
10. The method of claim 1, wherein the andrographolide is present in an amount of from about 0.001 to about 1%.

* * * * *